(12) United States Patent
Ishikawa et al.

(10) Patent No.: US 11,167,060 B2
(45) Date of Patent: Nov. 9, 2021

(54) METHOD FOR PRODUCING CALCIUM CARBONATE BLOCK

(71) Applicant: KYUSHU UNIVERSITY, NATIONAL UNIVERSITY CORPORATION, Fukuoka (JP)

(72) Inventors: Kunio Ishikawa, Fukuoka (JP); Kanji Tsuru, Fukuoka (JP); Akira Tsuchiya, Fukuoka (JP); Yuki Sugiura, Fukuoka (JP); Noriko Tanaka, Fukuoka (JP); Yasuharu Nakashima, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 16/495,246

(22) PCT Filed: Mar. 15, 2018

(86) PCT No.: PCT/JP2018/010193
§ 371 (c)(1),
(2) Date: Dec. 2, 2019

(87) PCT Pub. No.: WO2018/173915
PCT Pub. Date: Sep. 27, 2018

(65) Prior Publication Data
US 2020/0093955 A1 Mar. 26, 2020

(30) Foreign Application Priority Data
Mar. 21, 2017 (JP) .............................. JP2017-054398

(51) Int. Cl.
*C01F 11/18* (2006.01)
*C01B 25/16* (2006.01)
*A61L 27/08* (2006.01)

(52) U.S. Cl.
CPC .............. *A61L 27/08* (2013.01); *C01B 25/16* (2013.01); *C01F 11/181* (2013.01);
(Continued)

(58) Field of Classification Search
None
See application file for complete search history.

(56) References Cited

U.S. PATENT DOCUMENTS

| 5,558,850 A | 9/1996 | Bleakley et al. |
| 2001/0054253 A1* | 12/2001 | Takahashi .............. A01G 33/00 47/63 |
| 2017/0210635 A1 | 7/2017 | Ishikawa et al. |

FOREIGN PATENT DOCUMENTS

| JP | 5-501702 A | 4/1993 |
| JP | 4854300 B2 | 11/2011 |

(Continued)

OTHER PUBLICATIONS

International Search Report, International Patent Office, Application No. PCT/JP2018/010193, dated Apr. 17, 2018.

(Continued)

*Primary Examiner* — Daniel Berns
(74) *Attorney, Agent, or Firm* — Greenblum & Bernstein P.L.C.

(57) ABSTRACT

To provide a method for producing a calcium carbonate block for medical use which is useful as a bone substitute or a bone substitute raw material needed in medical care, which is a method for producing a calcium carbonate block that satisfies the following desired properties: 1) the calcium carbonate block has excellent mechanical strength; 2) the calcium carbonate block can be produced by a simplified production method; 3) the calcium carbonate block contains no impurity; and 4) the calcium carbonate block has high reactivity.

(Continued)

A method for producing a calcium carbonate block, comprising a step of shaping a water-containing calcium hydroxide block and a carbonation step of immersing the calcium hydroxide block in a carbonate ion-containing aqueous solution.

11 Claims, 2 Drawing Sheets

(52) U.S. Cl.
CPC .......... *C01F 11/182* (2013.01); *C01F 11/185* (2013.01); *A61L 2430/02* (2013.01); *C01P 2004/03* (2013.01)

(56) References Cited

FOREIGN PATENT DOCUMENTS

| | | |
|---|---|---|
| KR | 940018333 | 8/1994 |
| WO | 2016/052502 A1 | 4/2016 |
| WO | 2017/038360 A1 | 3/2017 |

OTHER PUBLICATIONS

International Preliminary Report on Patentability, International Patent Office, Application No. PCT/JP2018/010193, dated Sep. 24, 2019.
European Office Action, European Patent Office, Application No. 18771062.9, dated Dec. 11, 2020.

\* cited by examiner

[Figure 1]
a) In the case of water-containing calcium hydroxide block
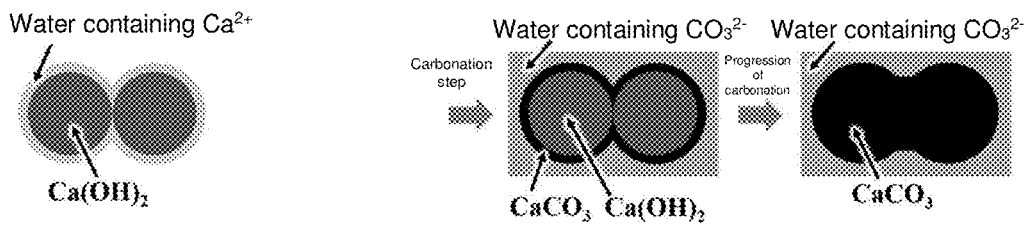
b) In the case of calcium hydroxide block containing substantially no water
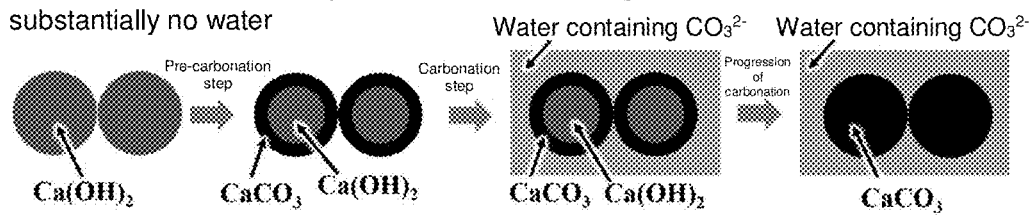
[Figure 2]
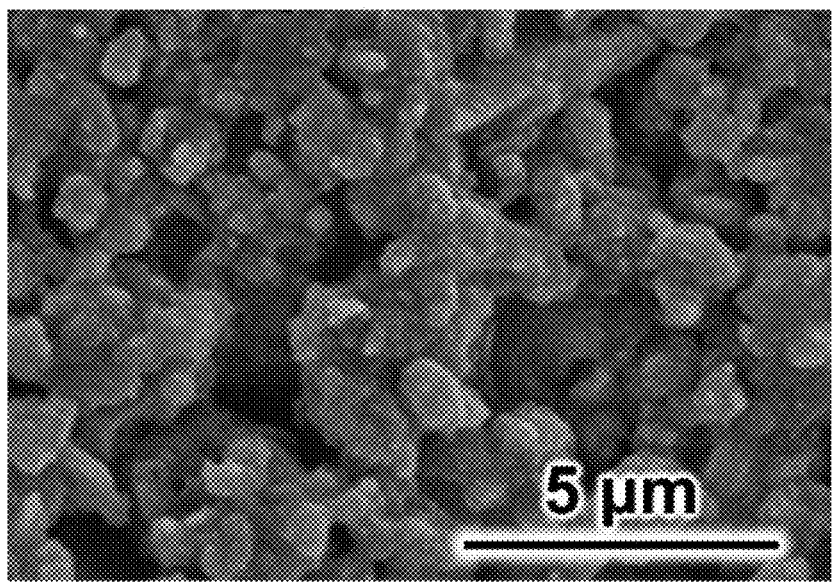

[Figure 3]
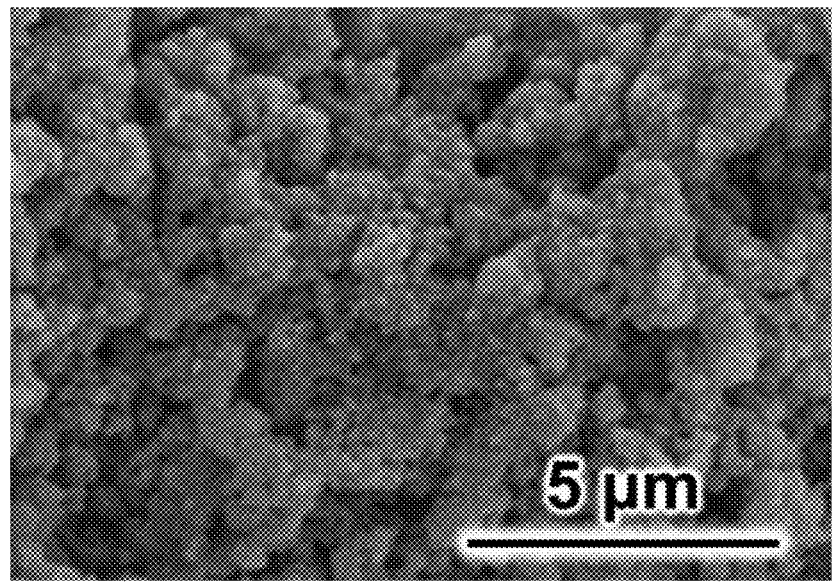
[Figure 4]
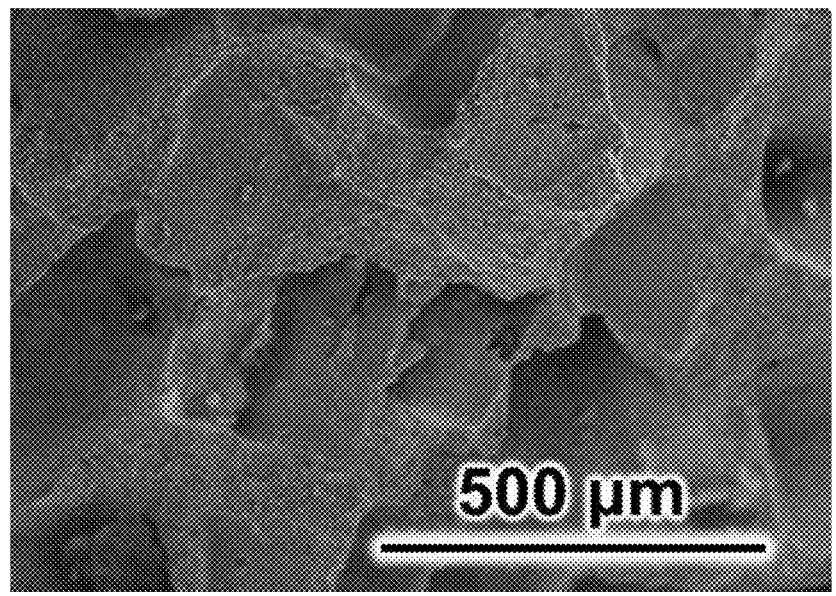

METHOD FOR PRODUCING CALCIUM CARBONATE BLOCK

TECHNICAL FIELD

The present invention relates to a method for producing a calcium carbonate block suitable for medical purposes. Particularly, the present invention relates to a method for producing a calcium carbonate block that satisfies the following properties required for medical purposes: 1) the calcium carbonate block has excellent mechanical strength; 2) the calcium carbonate block can be produced by a simplified production method; 3) the calcium carbonate block contains no impurity; and 4) the calcium carbonate block has high reactivity. The calcium carbonate block of the present invention can be used for medical purposes as a bone substitute or the like or as a bone substitute raw material or the like.

BACKGROUND ART

The composition of the skeleton of invertebrates is calcium carbonate, and chemically treated coral containing calcium carbonate as composition is being clinically applied as a bone substitute. However, coral harvesting destroys the nature, and furthermore, coral is a natural product and therefore presents serious problems such as inevitable containment of unintended impurities. Therefore, artificially produced calcium carbonate blocks for medical use are demanded.

The calcium carbonate block for medical use may be used in an operative procedure where the calcium carbonate block is pressed against a bone defect site for implantation, or the like. Small mechanical strength renders the calcium carbonate block clinically less valuable. Hence, one of the desired properties important for the calcium carbonate block for medical use is that 1) the calcium carbonate block has excellent mechanical strength.

One of the serious problems of bone substitutes using coral as a raw material is unintended impurities. Thus, in the case of using an artificially produced calcium carbonate block as a bone substitute, unintended impurities become a serious problem. In the case of containing a composition having specified components, calcium hydroxide being a raw material of the calcium carbonate block can induce inflammatory response due to its high alkalinity, which becomes a serious problem, and therefore needs to be fully carbonated into calcium carbonate. Hence, one of the desired properties important for the calcium carbonate block for medical use is that 3) the calcium carbonate block contains no impurity.

The high reactivity of the calcium carbonate block is an important desired property, and relates with an osteoconductivity or resorbability. In the case of enhancing an osteoconductivity or accelerating resorbability, it is necessary to produce the calcium carbonate block using calcium carbonate having high reactivity or low crystallinity. Hence, one of the desired properties important for the calcium carbonate block for medical use is that 4) the calcium carbonate block has high reactivity.

As described above, the skeleton of invertebrates is calcium carbonate, whereas the skeleton of vertebrates is carbonate apatite. Autologous bone containing carbonate apatite as composition is the first choice for a bone reconstructive technique, but presents serious problems associated with autologous bone collection. Allogeneic bone or xenogeneic bone presents serious problems such as unknown infection. Although carbonate apatite powders can be produced, carbonate apatite implanted in a powder state in vivo may be phagocytized by foreign-body giant cells and induce inflammatory response. In the 1970s, it was found that: hydroxyapatite powders that excluded carbonate group from carbonate apatite, a dominant inorganic component of bone, can be sintered; and that the hydroxyapatite ceramics exhibit an osteoconductivity. The hydroxyapatite ceramics is a typical bone substitute even now. Unlike autologous bone which replaces to bone, the hydroxyapatite ceramics does not substantially replace to bone even when implanted inside a bone defect. Since hydroxyapatite also serves as an adsorbent, problems such as the induction of inflammation due to postoperative infection are also pointed out.

The present inventors have proposed that a carbonate apatite block can be produced through dissolution-precipitation-type compositional transformation reaction using a precursor (see Patent Literature 1). In the case of using, for example, a calcium carbonate block as a precursor, when the calcium carbonate block is immersed in a phosphate aqueous solution, the composition of the calcium carbonate block is transformed into carbonate apatite through dissolution-precipitation-type compositional transformation reaction while maintaining its morphology.

The mechanical strength of the carbonate apatite block is closely related to the mechanical strength of the precursor calcium carbonate block. In other words, in the dissolution-precipitation-type compositional transformation reaction, the calcium carbonate block is compositionally transformed into carbonate apatite while basically maintaining its morphology. Therefore, only a carbonate apatite block having small mechanical strength is produced when the calcium carbonate block has small mechanical strength. Hence, one of the desired properties important for the calcium carbonate block for medical use is that 1) the calcium carbonate block has excellent mechanical strength.

If the calcium carbonate block contains unintended impurities, produced carbonate apatite also contains unintended impurities and is therefore unsuitable as the calcium carbonate block for medical use. A calcium carbonate block containing impurities comprising unknown components, or a component that induces detrimental effects on tissues is unsuitable as calcium carbonate for medical use, as a matter of course. The calcium carbonate block for medical use, etc. in carbonate apatite block production may present problems even when calcium hydroxide which components are known is contained therein.

When a calcium carbonate block containing calcium hydroxide as impurities is immersed in a phosphate aqueous solution, calcium carbonate is compositionally transformed into carbonate apatite while calcium hydroxide is compositionally transformed into hydroxyapatite. Therefore, a pure carbonate apatite block cannot be produced, but a block of carbonate apatite and hydroxyapatite mixture is produced. The carbonate apatite block containing hydroxyapatite does not replace to bone or takes time to replace to bone. Hence, one of the desired properties important for the calcium carbonate block for medical use is that 3) the calcium carbonate block contains no impurity.

In the case of producing a carbonate apatite block through dissolution-precipitation reaction using a calcium carbonate block as a precursor, it is important to use calcium carbonate having high reactivity, i.e., calcium carbonate having low crystallinity. For the dissolution-precipitation-type compositional transformation reaction, a dissolution process is essential. A calcium carbonate block having high crystallinity is inferior in reactivity including solubility and therefore takes time for compositional transformation when immersed in a phosphate solution, leading to high production cost or too long reaction time. Thus, the carbonate apatite block cannot substantially be produced in some cases. Hence, one of the desired properties important for the calcium carbonate block for medical use is that 4) the calcium carbonate block has high reactivity.

For the production of the calcium carbonate block for medical use, it is also desirable that 2) the calcium carbonate block can be produced by a simplified production method, from the viewpoint of production cost, etc.

Thus, it is desirable that the calcium carbonate block for medical use satisfies the following desired properties: 1) the calcium carbonate block has excellent mechanical strength; 2) the calcium carbonate block can be produced by a simplified production method; 3) the calcium carbonate block contains no impurity; and 4) the calcium carbonate block has high reactivity, from the viewpoint of medical needs and simplified production steps.

Under these circumstances, the present inventors have proposed a method for producing a calcium carbonate block focused on the following properties: 3) the calcium carbonate block contains no impurity; and 4) the calcium carbonate block has high reactivity, among the following desired properties required for a calcium carbonate block for medical use: 1) the calcium carbonate block has excellent mechanical strength; 2) the calcium carbonate block can be produced by a simplified production method; 3) the calcium carbonate block contains no impurity; and 4) the calcium carbonate block has high reactivity (Patent Literature 2).

The invention described therein provides a method for producing a calcium carbonate block, comprising:
(a) a calcium hydroxide block shaping step;
(b) a carbon dioxide contact step; and
(c) a carbonate ion-containing aqueous solution immersing step.

CITATION LIST

Patent Literature

Patent Literature 1: Japanese Patent No. 4854300
Patent Literature 2: International Publication No. WO 2016/052502

SUMMARY OF INVENTION

Technical Problem

An object of the present invention is to provide a method for producing a calcium carbonate block that satisfies the following many desired properties: 1) the calcium carbonate block has excellent mechanical strength; 2) the calcium carbonate block can be produced by a simplified production method; 3) the calcium carbonate block contains no impurity; and 4) the calcium carbonate block has high reactivity, which are required for a calcium carbonate block for medical use, or a calcium carbonate block useful as a precursor in the production of a carbonate apatite block for medical use.

Solution to Problem

As described above, the present inventors have proposed a method for producing a calcium carbonate block focused, particularly, on the following properties: 3) the calcium carbonate block contains no impurity; and 4) the calcium carbonate block has high reactivity, among the desired properties required for a calcium carbonate block for medical use (Patent Literature 2).

Specifically, this method is a method comprising:
(a) a calcium hydroxide block shaping step;
(b) a carbon dioxide contact step; and
(c) a carbonate ion-containing aqueous solution immersing step. A calcium carbonate block containing no impurity is produced even if unreacted calcium hydroxide is remained when a calcium hydroxide block is contacted with carbon dioxide to partially carbonate the surface of the block, since it reacts with the carbonate ions in the solution when the block is immersed in a carbonate ion-containing aqueous solution.

For this method, the carbon dioxide contact step (b), i.e., a pre-carbonation step, is an essential step. An object of this step is to confer morphological stability by contacting a shaped calcium hydroxide block containing substantially no water with carbon dioxide, and thereby partially carbonating the surface of the block. In the case of a calcium hydroxide block containing substantially no water, the shaped calcium hydroxide block disintegrates and cannot maintain its morphology when the block is immersed in a carbonate ion-containing aqueous solution. Therefore, the carbon dioxide contact step is essential for preventing the block from disintegrating by immersing in a carbonate ion-containing aqueous solution.

Hence, this method has a limited level of satisfaction for the following desired property required for a calcium carbonate block for medical use: 2) the calcium carbonate block can be produced by a simplified production method. Furthermore, this method cannot sufficiently satisfy, in some cases, the following desired property: 1) the calcium carbonate block has excellent mechanical strength.

Under these circumstances, the present inventors have further conducted the studies described above and consequently completed the present invention by finding that a water-containing calcium hydroxide block is immersed in a carbonate ion-containing aqueous solution to make the calcium carbonate block, whereby the conventional partial carbonation step can be omitted so that the method can be simplified, and furthermore, the mechanical strength of the produced calcium carbonate block is also drastically improved.

Specifically, the present invention is as follows.
[1] A method for producing a calcium carbonate block, comprising: a calcium hydroxide block shaping step of shaping a water-containing calcium hydroxide block; and a carbonation step of immersing the calcium hydroxide block in a carbonate ion-containing aqueous solution to make the calcium carbonate block.
[2] The method for producing a calcium carbonate block according to [1], comprising, between the calcium hydroxide block shaping step and the carbonation step, a pre-carbonation step of contacting the calcium hydroxide block with carbon dioxide to make a partially carbonated calcium hydroxide block.
[3] The method for producing a calcium carbonate block according to [1] or [2], further comprising: a pore-forming substance mixing step; and a pore formation step.
[4] The method for producing a calcium carbonate block according to any one of [1] to [3], wherein the water-containing calcium hydroxide block shaped in the calcium hydroxide block shaping step contains 4% by weight or more of water.

[5] The method for producing a calcium carbonate block according to any one of [1] to [4], wherein a volume of the calcium carbonate block obtained in the carbonation step is $10^{-13}$ m$^3$ or larger.

[6] The method for producing a calcium carbonate block according to any one of [1] to [5], wherein the carbonate ion-containing aqueous solution used in the carbonation step contains carbonate ion having a concentration of 0.1 mol/L or more.

[7] The method for producing a calcium carbonate block according to any one of [1] to [6], wherein pH of the carbonate ion-containing aqueous solution for use in the carbonation step is 6 or higher.

[8] A method for producing a carbonate apatite block, comprising imparting a phosphate solution to a calcium carbonate block produced by the method according to any one of [1] to [7].

Advantageous Effects of Invention

The method for producing a calcium carbonate block according to the present invention can produce a calcium carbonate block that is suitable for medical purposes and satisfies the following many desired properties: 1) the calcium carbonate block has excellent mechanical strength; 2) the calcium carbonate block can be produced by a simplified production method; 3) the calcium carbonate block contains no impurity; and 4) the calcium carbonate block has high reactivity.

BRIEF DESCRIPTION OF DRAWINGS

FIG. 1a) is a conceptual diagram showing the state of a block in each step of the production method of the present invention. FIG. 1b) is a conceptual diagram showing the state of a block in each step of a conventional production method.

FIG. 2 is a scanning electron microscopic image of a calcium carbonate block produced by immersing for 4 days in a sodium hydrogen carbonate aqueous solution in a carbonation step in Example 1.

FIG. 3 is a scanning electron microscopic image of a calcium carbonate block produced by immersing for 4 days in a sodium hydrogen carbonate aqueous solution in a carbonation step in Comparative Example 3.

FIG. 4 is a scanning electron microscopic image of the cross section of a porous calcium carbonate block produced in Example 5.

DESCRIPTION OF EMBODIMENTS

<Essential Requirement for Present Invention>

The method for producing a calcium carbonate block according to the present invention comprises:

a calcium hydroxide block shaping step of shaping a water-containing calcium hydroxide block; and a carbonation step of immersing the calcium hydroxide block in a carbonate ion-containing aqueous solution to make the calcium carbonate block.

<Basic Mechanism of Present Invention>

The present inventors believe that according to the present invention, a calcium carbonate block that satisfies the following many desired properties: 1) the calcium carbonate block has excellent mechanical strength; 2) the calcium carbonate block can be produced by a simplified production method; 3) the calcium carbonate block contains no impurity; and 4) the calcium carbonate block has high reactivity, is produced under a basic mechanism as mentioned below. This basic mechanism is a mechanism considered valid at this time by the inventors. The present invention is not influenced by the validity, accuracy, etc. of the basic mechanism described below.

The basic mechanism of the present invention is that a calcium carbonate block is produced by a simple method which suppresses the disintegration property of the calcium hydroxide block by immersing a water-containing calcium hydroxide block in a carbonate ion-containing aqueous solution, and thereby immediately bridging calcium hydroxide powders through calcium carbonate, and also offers excellent mechanical strength by bridging calcium hydroxide powders at a wide area with the formed calcium carbonate, and fully carbonating the hydroxide calcium powders. Particularly, the bridging of calcium hydroxide powders at a wide area by carbonation in the presence of water is a mechanism important for the property: 1) the calcium carbonate block has excellent mechanical strength.

The carbonation of calcium hydroxide includes dry carbonation and wet carbonation. The basic reaction of calcium carbonate formation is described by (Formula 1) to (Formula 5).

(Dry Carbonation)

$$Ca(OH)_2 + CO_2 \rightarrow CaCO_3 + H_2O \qquad \text{(Formula 1)}$$

(Wet Carbonation)

$$Ca(OH)_2 \rightarrow Ca^{2+} + 2OH^- \qquad \text{(Formula 2)}$$

$$CO_2 + H_2O \rightarrow CO_3^{2-} + 2H^+ \qquad \text{(Formula 3)}$$

$$Ca^{2+} + CO_3^{2-} \rightarrow CaCO_3 \qquad \text{(Formula 4)}$$

$$Ca(OH)_2 + CO_2 \rightarrow CaCO_3 + H_2O \qquad \text{(Formula 5)}$$

The dry carbonation is a direct carbonation reaction that requires no water, but requires a high temperature. In the dry carbonation, as shown in (Formula 1), calcium hydroxide and carbon dioxide react directly with each other at approximately 270° C. or higher to form calcium carbonate. Because of using a high temperature, the formed calcium carbonate has high crystallinity and low reactivity. Hence, the following property required for a calcium carbonate block for medical use: 4) the calcium carbonate block has high reactivity cannot be satisfied if the whole carbonation of the calcium hydroxide block is performed by this dry process.

On the other hand, the wet carbonation requires water, but requires no high temperature. Hence, a calcium carbonate having low crystallinity and high reactivity can be produced.

The formation of calcium carbonate by the wet carbonation is basically ionic reaction. Since water or moisture is present, calcium hydroxide and carbon dioxide are ionized as shown in (Formula 2) and (Formula 3) to form calcium ions and carbonate ions. The calcium ions and the carbonate ions form calcium carbonate through the ionic reaction of (Formula 4). As a result, as shown in (Formula 5) which summarizes (Formula 2) to (Formula 4), calcium carbonate is formed from calcium hydroxide and carbon dioxide in the presence of water.

Among the following desired properties of a calcium carbonate block for medical use: 1) the calcium carbonate block has excellent mechanical strength; 2) the calcium carbonate block can be produced by a simplified production method; 3) the calcium carbonate block contains no impurity; and 4) the calcium carbonate block has high reactivity, the property: 4) the calcium carbonate block has high reactivity is achieved by the wet carbonation. In order to further satisfy the properties: 1) the calcium carbonate block has excellent mechanical strength; 2) the calcium carbonate block can be produced by a simplified production method; and 3) the calcium carbonate block contains no impurity, the following objects had to be overcome.

Firstly, a calcium hydroxide compact containing substantially no water disintegrate and cannot maintain its morphology when immersed in a carbonate ion-containing aqueous solution.

Secondly, the calcium hydroxide compact containing substantially no water is very difficult to fully carbonate, though the carbonation progresses chronologically by contact with carbon dioxide at a relative humidity of 100%.

Thirdly, when the calcium hydroxide compact containing substantially no water is contacted with carbon dioxide at a relative humidity of 100% for the carbonation progresses, followed by immersion in a carbonate ion-containing aqueous solution, a calcium carbonate block which is completely calcium carbonate can be produced without comprising calcium hydroxide. However, the mechanical strength of the calcium carbonate block is limited.

Fourthly, a water-containing calcium hydroxide block is less likely to be carbonated even when being in contact with carbon dioxide at a relative humidity of 100%.

Fifthly, a pre-carbonation step, if essential, impairs the simplification of production steps.

The present invention overcomes these objects by the basic mechanism that "a calcium carbonate block for medical use also having excellent mechanical strength is produced by a simple method comprising immersing a water-containing calcium hydroxide block in a carbonate ion-containing aqueous solution, to immediately bridging calcium hydroxide powders with calcium carbonate to suppress the disintegration property of the calcium hydroxide block, and bridging calcium hydroxide powders at a wide area with the formed calcium carbonate, and fully carbonating the hydroxide calcium powders". The present invention provides a calcium carbonate block that is suitable for medical purposes and satisfies the following desired properties: 1) the calcium carbonate block has excellent mechanical strength; 2) the calcium carbonate block can be produced by a simplified production method; 3) the calcium carbonate block contains no impurity; and 4) the calcium carbonate block has high reactivity.

In this context, FIG. 1 shows a conceptual diagram of the basic mechanism of the present invention. As shown in FIG. 1a), calcium hydroxide is dissolved, albeit in a very small amount, in water to form calcium ions. Hence, the water-containing calcium hydroxide block produced in the calcium hydroxide block shaping step is a water-containing calcium hydroxide block containing calcium ions.

When this block is immersed in a carbonate ion-containing aqueous solution, as shown in (Formula 4), the calcium ions and the carbonate ions react immediately with each other to form calcium carbonate on calcium hydroxide powder surface. Thus, the calcium hydroxide powders are bridged with the calcium carbonate. As a result, the block can maintain its morphology without disintegrating, even when immersed in a carbonate ion-containing aqueous solution.

Then, the calcium ions formed by the dissolution of calcium hydroxide, and the carbonate ions ionically react with each other, as shown in (Formula 4), to form calcium carbonate. Because it is a calcium carbonate formation in water, the calcium carbonate crystals easily grow large, and the calcium hydroxide powders are bridged at a wide area through the formed calcium carbonate. As a result, a calcium carbonate block having excellent mechanical strength can be produced.

In the water-containing calcium hydroxide block, water is present in the gaps between the calcium hydroxide powders. Hence, the fact that the effect to detach the powders from each other due to water penetrating into the gaps between the powders is small when the block is immersed in water, is also considered to be one of the reasons why the block does not disintegrate without pre-carbonation even when immersed in water containing carbonate ions.

On the other hand, when the calcium hydroxide block containing substantially no water is immersed in water containing carbonate ions, water containing carbonate ions penetrates into the gaps between the calcium hydroxide powders constituting the calcium hydroxide block and detaches the powders from each other. Hence, the calcium hydroxide block disintegrate when the block is immersed, without pre-carbonation, in water containing carbonate ions.

Accordingly, as shown in FIG. 1b), the pre-carbonation step is essential for pre-carbonating the calcium hydroxide block containing substantially no water so as not to disintegrate by immersing in water containing carbonate ions. Hence, one more production step is always necessary.

Furthermore, the contact area between the calcium hydroxide powders with the formed calcium carbonate is limited, as shown in FIG. 1b), because pre-carbonation progresses under conditions where water is not sufficiently present. Hence, the mechanical strength of the produced calcium carbonate block is limited.

<Detailed Description of the Invention>

Hereinafter, the present invention will be described in detail.

<Calcium Hydroxide Block Shaping Step>

In the calcium hydroxide block shaping step, a water-containing calcium hydroxide block is shaped.

(Calcium Hydroxide Powder)

A raw material calcium hydroxide can be used without particular limitations as long as the raw material contains no impurity. In order to achieve an intended purpose, another substance may be mixed with calcium hydroxide to form a block shape.

For example, hydroxyapatite, carbonate apatite, β-tricalcium phosphate, or calcium sulfate can be mixed therewith with the aim of improving an osteoconductivity, etc.

(Shaping of Water-Containing Calcium Hydroxide Block)

The water-containing calcium hydroxide block is shaped by a method of malaxating calcium hydroxide powders with water, a method of spraying water onto calcium hydroxide powders, or the like. Shapeability appears in the calcium hydroxide powders in the presence of water. Therefore, powder compacting, etc. is not necessarily required as in the case of shaping of the calcium hydroxide block containing substantially no water. However, in an effective approach, the water-containing calcium hydroxide powders are placed in a mold, if necessary, and compacted for shaping. The powder compacting removes an excess of water from the calcium hydroxide block and therefore decreases a porosity, and thus, is particularly suitable for improvement in mechanical strength.

The shaping pressure can be appropriately set according to the balance between the mechanical strength and porous body formation of the resulting block, and is for example, preferably 5 to 100 MPa, more preferably 7 to 70 MPa, further preferably 10 to 50 MPa, and particularly preferably 15 to 50 MPa.

(Water Content in Water-Containing Calcium Hydroxide Block)

The water content ratio of the calcium hydroxide block is preferably 1% by weight or more, more preferably 4% by weight or more, further preferably 6% by weight or more, particularly preferably 8% by weight or more, most preferably 10% by weight or more, from the viewpoint of efficiently exerting the effect of carbonating calcium hydroxide powders in the presence of a sufficient amount of water, and bridging the calcium hydroxide powders at a wider area with the formed calcium carbonate. On the other hand, the water content ratio of the calcium hydroxide block is preferably 70% by weight or less, more preferably 60% by weight or less, further preferably 50% by weight or less, from the viewpoint of insuring favorable handling property of the calcium hydroxide block.

Approximately 0.4% by weight of water is adsorbed onto general calcium hydroxide powders because the calcium hydroxide powders are not hygroscopic.

The water content in the calcium hydroxide block can be calculated, for example, by drying the calcium hydroxide block at 100° C. for 3 hours under nitrogen to fully evaporate water in the calcium hydroxide block, and measuring the weights before and after the drying.

(Size of Calcium Hydroxide Block)

In the present invention, the volume of the produced calcium carbonate block is preferably $10^{-13}$ m$^3$ or larger. The volume of the calcium hydroxide block produced in this step is not totally the same as that of a calcium carbonate block produced as a final product. However, usually, the volume of the calcium hydroxide block produced in this step is equivalent to that of a calcium carbonate block as a final product. The size of the calcium hydroxide block to be shaped can be determined with attention to the fact that the block may be pulverized into granules, for example.

The size of the shaped block is preferably a diameter (diagonal line) of 0.1 cm to 50 cm and a thickness of 0.1 cm to 5 cm, more preferably a diameter (diagonal line) of 3 cm to 10 cm and a thickness of 1 cm to 2 cm. Examples of the shape of the block include, but are not particularly limited to, cylindrical columns, rectangular parallelepipeds, and in form of plates.

<Pre-Carbonation Step>

The pre-carbonation step is a step of contacting the calcium hydroxide block with carbon dioxide to make a partially carbonated calcium hydroxide block. This step is performed, if necessary, in the production method of the present invention.

(Purpose of Pre-Carbonation Step)

When the calcium hydroxide block is immersed in a carbonate ion-containing aqueous solution by a method such as immersing, two events progress competitively.

One of the events is the penetration of water into the gaps between the powders constituting the calcium hydroxide block. Water acts to detach the powders from each other. The calcium hydroxide block disintegrates and cannot maintain its morphology when water that has penetrated into the gaps between the calcium hydroxide powders detaches the calcium hydroxide powders from each other.

The other event is the formation of calcium carbonate through the ionic reaction of the carbonate ions of the carbonate ion-containing aqueous solution with the calcium ions in water of the water-containing calcium hydroxide block. The formed calcium carbonate bridges the calcium hydroxide powders. The calcium hydroxide block bridged by calcium carbonate does not disintegrate even in water.

Both events progress competitively. There are cases that even the water-containing calcium hydroxide block cannot maintain its complete morphology, depending on production conditions, when the calcium hydroxide block is immersed in a carbonate ion-containing aqueous solution. Also, there are cases that mechanical strength of the calcium carbonate became small due to the penetration of water into the gaps between the calcium hydroxide powders.

There is no problem, for example, to produce calcium carbonate granules by pulverizing the calcium carbonate block even when the calcium hydroxide block cannot maintain its complete morphology. However, by performing the pre-carbonation, the disintegration of the calcium hydroxide block when immersed in a carbonate ion-containing aqueous solution can be totally suppressed.

When the water-containing calcium hydroxide block contain a calcium salt, effectiveness for suppressing the disintegration of the block became high because a high calcium ion concentration increases the amount of calcium carbonate formed through reaction with water containing carbonate ions.

Although it may be preferred to perform the pre-carbonation step in some cases, the pre-carbonation step disadvantageously increases the number of production steps. In some cases, the disintegration of the block is not necessarily required to be totally suppressed. Hence, whether or not to perform the pre-carbonation step is determined from the balance between these two factors.

(Method of Contacting Calcium Hydroxide Block with Carbon Dioxide)

The contact of the calcium hydroxide block with carbon dioxide can be attained by merely placing the calcium hydroxide block in a carbon dioxide environment. Examples of the carbon dioxide environment include a method using a carbon dioxide incubator. Although the carbonation conditions depend on the size of the block, the shaping pressure, etc., the carbonation conditions such as carbon dioxide concentration, relative humidity, and temperature can be properly controlled by using the carbon dioxide incubator.

The conditions for the contact of the calcium hydroxide block with carbon dioxide are not particularly limited. The carbon dioxide concentration is preferably 5% to 100% in relation to a production time. The relative humidity needs to exceed 0% from the viewpoint of preventing rapid evaporation of water contained in the calcium hydroxide block. The relative humidity is preferably 50% to 100%, more preferably 80% to 100%, further preferably 90% to 100%, from the viewpoint of efficient wet carbonation and the prevention of water evaporation from the block.

The temperature is preferably 0° C. to 80° C. from the viewpoint of a production time. At a lower temperature, calcium carbonate having lower crystallinity and higher reactivity can be produced.

The carbonation time is appropriately determined depending on the temperature when contacting the calcium hydroxide block with carbon dioxide, the size of the calcium hydroxide block, etc., and is, for example, 1 minute to 300 hours.

<Carbonation Step>

The carbonation step is a step of immersing the calcium hydroxide block in a carbonate ion-containing aqueous solution to make the calcium carbonate block. The calcium hydroxide block can be a partially carbonated calcium hydroxide block having undergone the above-mentioned pre-carbonation step.

(Purpose of Carbonation Step)

The purpose of the carbonation step is to "bridge calcium hydroxide powders at a wide area through the formed calcium carbonate and fully carbonate the calcium hydroxide powders" by reacting calcium ions formed from calcium hydroxide with carbonate ions contained in the carbonate ion-containing aqueous solution, in water.

In the present invention, the water-containing calcium hydroxide block is used. Therefore, in the case of performing a pre-carbonation step, the calcium ions and the carbonate ions also react with each other in the presence of a sufficient amount of water to form calcium carbonate. In the carbonation step as well, the calcium ions and the carbonate ions also react with each other in the presence of a sufficient amount of water to form calcium carbonate.

The carbonation of the water-containing calcium hydroxide block is much less likely to progress by the pre-carbonation step, as compared with a calcium hydroxide block containing substantially no water. This is probably because, in the case of a water-containing calcium hydroxide block, the diffusion of carbon dioxide to the inside of the block is inhibited by water even when the block is contacted with carbon dioxide. However, in the case of the water-containing calcium hydroxide block, the pre-carbonation step is inherently not essential. In the case of performing a pre-carbonation step, the calcium hydroxide block can be fully carbonated by the subsequent carbonation step, as a matter of course.

(Carbonate Ion-Containing Aqueous Solution)

In the carbonation step, a sufficient amount of water is present because the calcium hydroxide block is immersed in a carbonate ion-containing aqueous solution. Therefore, calcium carbonate crystals formed on calcium hydroxide particle surface can grow in water. Thus, the calcium hydroxide particles are contacted with each other on a larger face to produce a calcium carbonate block having excellent mechanical strength.

Since water is present in the carbonation step, the carbonate ions can be supplied at a sufficient rate to calcium hydroxide. Furthermore, the carbonate ion concentration or the absolute amount of the carbonate ions can be elevated. Thus, calcium hydroxide can be fully carbonated to produce a calcium carbonate block containing no calcium hydroxide.

(Carbonate Ion Concentration of Carbonate Ion-Containing Aqueous Solution)

In the carbonation step, the carbonate ion concentration can be elevated because the carbonate ion-containing aqueous solution is used. A higher carbonate ion concentration accelerates the calcium carbonate formation reaction of (Formula 4). Therefore, the carbonate ion concentration of the carbonate ion-containing aqueous solution in the carbonation step is preferably 0.1 mol/L or higher, more preferably 0.3 mol/L or higher, further preferably 0.6 mol/L or higher.

(pH of Carbonate Ion-Containing Aqueous Solution)

While the carbonate ion-containing aqueous solution is used in the carbonation step, carbon dioxide differs in the state of presence in water depending on pH, and is present as carbonic acid ($H_2CO_3$), hydrogen carbonate ions ($HCO^{3-}$), or carbonate ions ($CO_3^{2-}$). The hydrogen carbonate ions and the carbonate ions react with the calcium ions to form calcium carbonate. The presence ratios of the hydrogen carbonate ions and the carbonate ions are small when the pH is low. Therefore, the pH of the carbonate ion-containing aqueous solution in the carbonation step is preferably 6 or higher, more preferably 7 or higher, further preferably 8 or higher.

The solution containing these carbonate ions can be produced by dissolving, for example, sodium hydrogen carbonate, sodium carbonate, potassium hydrogen carbonate, potassium carbonate, ammonium hydrogen carbonate, or ammonium carbonate in water.

(Temperature of Carbonate Ion-Containing Aqueous Solution)

A higher temperature of the aqueous solution is more preferred from the viewpoint of the carbonation reaction rate of calcium hydroxide. On the other hand, calcium carbonate having high crystallinity and low reactivity is produced when the aqueous solution has a high temperature. The temperature of the carbonate ion-containing aqueous solution is preferably 5° C. to 95° C., more preferably 10° C. to 90° C., further preferably 15° C. to 80° C., from the balance between these two factors.

(Washing and Drying of Calcium Carbonate Block)

The produced calcium carbonate block can be washed and dried by general methods after the carbonation step. As for the washing, for example, the surface can be rinsed with distilled water and then further immersed in distilled water to remove the components or the like of the carbonate ion-containing aqueous solution used in the carbonation step. For example, the calcium carbonate block thus washed can be dried at 60° C. for 24 hours to remove water from the water-containing calcium carbonate block.

(Volume of Produced Calcium Carbonate Block for Medical Use)

The volume of the calcium carbonate block produced by the production method of the present invention is preferably $10^{-13}$ $m^3$ or larger. This is because the calcium carbonate block of the present invention is used as a bone substitute or a precursor for bone substitute production. Upon implantation of the powders in vivo, macrophages are activated, and the macrophages release cytokines. Foreign-body giant cells are activated by the cytokines and thereby phagocytize the powders, and induce inflammatory response. The implanted calcium carbonate block having a volume of $10^{-13}$ $m^3$ or larger can suppress the induction of inflammatory response.

The volume of the calcium carbonate block produced by the production method of the present invention is more preferably $10^{-12}$ $m^3$ or larger, further preferably $10^{-11}$ $m^3$ or larger, particularly preferably $10^{-10}$ $m^3$ or larger, from the viewpoint of more reliably suppressing the induction of inflammatory response.

In the present invention, the volume of the calcium carbonate block is defined as the amount that the calcium carbonate block occupies in a three-dimensional space. Specifically, in the case of a porous block, an apparent volume including air and the like inside the porous block is regarded as the volume described in the present invention.

<Pore-Forming Substance Mixing Step and Pore Formation Step>

The pore-forming substance mixing step and the pore formation step are the steps that are provided when producing a porous calcium carbonate block.

(Mixing of Water-Containing Calcium Hydroxide Block with Pore-Forming Substance)

The porous calcium carbonate block can be produced by mixing the water-containing calcium hydroxide block with a pore-forming substance. The porous calcium carbonate block can be produced by undergoing the production steps of the pore-forming substance mixing step, the calcium hydroxide block shaping step, the carbonation step, and the pore formation step.

The pore-forming substance can be appropriately selected as long as the pore-forming substance is soluble in a solvent for use in the pore formation step. Examples thereof include sodium chloride and saccharides when the solvent is water.

The pore-forming substance mixing step is a step of mixing the raw material calcium hydroxide with a substance (pore-forming substance) soluble in a specific solvent. This pore-forming substance mixing step and a pore formation step mentioned later enable to obtain a porous calcium carbonate block throughout which pores are distributed. The mixing volume ratio between calcium hydroxide and the pore-forming substance is preferably 2:1 to 1:2. The size of the pore-forming substance serves as the size of the pores to be formed and can therefore be appropriately selected. The size is preferably 10 μm to 1000 μm, more preferably 30 μm to 500 μm, further preferably 50 μm to 300 μm.

In the pore-forming substance mixing step, water can be added after mixing the pore-forming substance and calcium hydroxide, or the pore-forming substance can be mixed with the water-containing calcium hydroxide. It is effective to dissolve the pore-forming substance in advance in water to be mixed with the calcium hydroxide block in order to prevent morphological change or the like caused by the dissolution of the pore-forming substance in water. The concentration at which the pore-forming substance is dissolved is not particularly limited. The pore-forming substance is preferably saturated in water.

The pore formation step is a step of dissolving the pore-forming substance in the block in water or the like to form pores. This step may be independently performed or may be performed at the same time with the carbonation step.

<Method for Producing Carbonate Apatite Using Calcium Carbonate of the Present Invention as Raw Material>

The calcium carbonate block obtained by the method for producing a calcium carbonate block according to the present invention is a calcium carbonate block containing no impurity, as described above. Therefore, a carbonate apatite block containing no impurity and also having excellent mechanical strength can be produced by imparting (adding) a phosphate solution to the calcium carbonate block, and reacting them. Examples of the method for imparting a phosphate solution to the calcium carbonate block can include a method of immersing the calcium carbonate block in the phosphate solution, and a method of spraying the phosphate solution onto the calcium carbonate block.

EXAMPLES

Hereinafter, the method for producing a calcium carbonate block according to the present invention will be specifically described with reference to examples. However, the present invention is not limited by these examples. In the present Examples and Comparative Examples, studies were made under conditions described below.

The water content ratio of the calcium hydroxide block was calculated as the content ratio of water contained in the calcium hydroxide block by drying the calcium hydroxide block at 100° C. for 3 hours under nitrogen, and thereby evaporating moisture.

The contact of the calcium hydroxide block with carbon dioxide in the pre-carbonation step was performed using a carbon dioxide contact apparatus. The carbon dioxide contact apparatus supplies 200 mL/min of carbon dioxide gas having an adjusted relative humidity from a gas inlet of a container (capacity: 19 L), and discharges excess carbon dioxide from a gas outlet.

The contact of the calcium hydroxide block with a carbonate ion-containing aqueous solution in the carbonation step was performed by immersing the calcium hydroxide block in a 80° C. 1 mol/L sodium hydrogen carbonate aqueous solution. The pH of the 1 mol/L sodium hydrogen carbonate aqueous solution was 8.6.

The rate of carbonation of the calcium hydroxide block was calculated by using a powder X-ray diffraction apparatus (D8 Advance) manufactured by Bruker Corp., and quantifying the molar ratio of calcium hydroxide and calcium carbonate from peak areas attributed to calcium hydroxide ($2\theta=34.2$ degrees) and calcium carbonate ($2\theta=29.4$ degrees).

The powder X-ray diffraction as well as a more highly sensitive phenolphthalein test were conducted to confirm that the calcium hydroxide block became a calcium carbonate composition completely. Phenolphthalein is clear and colorless, but gives a red color in alkalinity, and therefore gives a red color when alkaline calcium hydroxide remains. Therefore, the block was divided, and a phenolphthalein solution was added dropwise to the exposed central part to confirm whether or not to be colored red.

In the present invention, a sample colored red is regarded as being in the phenolphthalein test positive, and a sample not colored red is regarded as being in the phenolphthalein test negative.

The diametral tensile strength of the calcium hydroxide block was measured as an index for the mechanical strength of the calcium hydroxide block using a universal testing machine (model AGS-J) manufactured by Shimadzu Corp. The sample was crashed at a crosshead speed of 10 mm/min, and the diametral tensile strength was measured from the maximum load reaching the crash.

Example 1

<Calcium Hydroxide Block Shaping Step>

Calcium hydroxide (manufactured by Wako Pure Chemical Industries, Ltd.) and distilled water were mixed at a water/powder mixing ratio of 1.13. The mixture was uniaxially press-shaped at 20 MPa using a mold to shape a calcium hydroxide compact having a diameter of 6 mm and a height of 3 mm. A portion of water was discharged during the uniaxial pressurization. The water content ratio of the shaped calcium hydroxide block was 26% by weight.

<Pre-Carbonation Step>

The shaped calcium hydroxide compact was carbonated with carbon dioxide having a relative humidity of 100% using a carbon dioxide contact apparatus.

The rate of carbonation of the calcium hydroxide block after contact for 12 hours, 24 hours, and 48 hours with carbon dioxide in this apparatus was 18% by mol, 20% by mol, and 22% by mol, respectively.

Further, the diametral tensile strength of the calcium hydroxide block was 5.7 MPa, 6.8 MPa, and 7.9 MPa, respectively.

The pre-carbonation of the water-containing calcium hydroxide block was found to significantly improve the mechanical strength of the block, though the carbonation was significantly slow.

<Carbonation Step>

The water-containing calcium hydroxide block that underwent the carbonation step was immersed in a 80° C. 1 mol/L sodium hydrogen carbonate aqueous solution for 1 day and 4 days. Each block was rinsed with distilled water, and washed by immersing in 80° C. distilled water for 24 hours. Further, the block was dried at 60° C. for 24 hours.

The rate of carbonation of the calcium hydroxide block after immersion for 1 day and 4 days was 92% by mol and 100% by mol, respectively. The block after immersion for 4 days was phenolphthalein test negative. Thus, the block was found to be fully converted into calcium carbonate in which no calcium hydroxide remained.

The diametral tensile strength of the block was 8.1 MPa and 8.2 MPa, respectively.

FIG. 2 shows a scanning electron microscopic image of the calcium carbonate block for medical use of Example 1 produced by immersing in the sodium hydrogen carbonate aqueous solution for 4 days in the carbonation step. The powders were found to be bridged at a wide area by precipitates.

Example 2

<Calcium Hydroxide Block Shaping Step>

Calcium hydroxide (manufactured by Wako Pure Chemical Industries, Ltd.) and distilled water were mixed at a water/powder mixing ratio of 0.1. The mixture was uniaxially press-shaped at 20 MPa using a mold to shape a calcium hydroxide compact having a diameter of 6 mm and a height of 3 mm. The discharge of water was not observed during the uniaxial pressurization. The water content ratio of the shaped calcium hydroxide block was 9% by weight.

<Pre-Carbonation Step>

The pre-carbonation step was not performed.

<Carbonation Step>

The calcium hydroxide block containing 9% by weight of water was immersed in a 80° C. 1 mol/L sodium hydrogen carbonate aqueous solution for 4 days. Then, the block was rinsed with distilled water, and washed by immersing in 80° C. distilled water for 24 hours. Further, the block was dried at 60° C. for 24 hours.

The rate of carbonation of the calcium hydroxide block was 100% by mol, and the block was phenolphthalein test negative. Thus, the block was found to be fully converted into calcium carbonate in which no calcium hydroxide remained.

This demonstrated that the calcium hydroxide compact containing 9% by weight or more of water is carbonated into calcium carbonate while maintaining its morphology without disintegrating when immersed in the 1 mol/L sodium hydrogen carbonate aqueous solution, even if the pre-carbonation step is not performed.

The diametral tensile strength of the calcium carbonate block was 2.6 MPa.

On the other hand, the comparison between the results of Example 1 and Example 2 demonstrated that a carbonate apatite block having better mechanical strength can be produced by using a larger amount of water-containing calcium hydroxide, and performing pre-carbonation.

Comparative Example 1

For the purpose of revealing the need for the carbonation step in Example 1, the water-containing calcium hydroxide block shaped in Example 1 was carbonated only by the pre-carbonation step. This production method is a production method that falls out of the scope of the present invention because the carbonation step is not performed. The carbonation period in the pre-carbonation step was set to a total of 3 days and 6 days in which the carbonation period of the pre-carbonation period of Example 1, 1 day and 4 days, were added, respectively.

The calcium hydroxide compact was contacted with carbon dioxide for 3 days and 6 days using a carbon dioxide contact apparatus. Then, the block was rinsed with distilled water, and washed by immersing in 80° C. distilled water for 24 hours. Further, the block was dried at 60° C. for 24 hours.

The rate of carbonation of the block contacted with carbon dioxide for 3 days and 6 days was 27% by mol and 28% by mol, respectively. Thus, increase in the rate of carbonation was very limited even when the period of contact with carbon dioxide was prolonged.

The difference between the results of Example 1 and Comparative Example 1 demonstrated that the carbonation step is essential for producing the calcium carbonate block for medical use, whereas the pre-carbonation step alone merely produces a block in which calcium hydroxide remains.

Comparative Example 2

<Calcium Hydroxide Block Shaping Step>

Calcium hydroxide (manufactured by Wako Pure Chemical Industries, Ltd.) was uniaxially press-shaped at 20 MPa using a mold to shape a calcium hydroxide compact containing substantially no water and having a diameter of 6 mm and a height of 3 mm. The water content ratio of the shaped calcium hydroxide block was 0.4% by weight.

<Pre-carbonation Step>

The pre-carbonation step was not performed.

<Carbonation Step>

The calcium hydroxide block containing substantially no water was immersed in a 80° C. 1 mol/L sodium hydrogen carbonate aqueous solution.

The calcium hydroxide block disintegrated immediately after the immersion, and failed to maintain its morphology.

The pre-carbonation step was found to be essential for producing the calcium carbonate block using the calcium hydroxide block containing substantially no water.

Comparative Example 3

<Calcium Hydroxide Block Shaping Step>

A calcium hydroxide block containing substantially no water was produced by the same method as in Comparative Example 2.

<Pre-Carbonation Step>

The calcium hydroxide block was contacted with carbon dioxide having a relative humidity of 100% at 30° C. for 1 hour using a carbon dioxide contact apparatus.

The rate of carbonation of the partially carbonated calcium hydroxide block was 14% by mol, and the indirect tensile strength thereof was 1.3 MPa.

<Carbonation Step>

The calcium hydroxide block partially carbonated by the pre-carbonation step was immersed in a 80° C. 1 mol/L sodium hydrogen carbonate aqueous solution for 1 day and 4 days.

The rate of carbonation of the calcium hydroxide block after immersion for 1 day and 4 days was 94% by mol and 100% by mol, respectively.

The block thus immersed for 4 days was phenolphthalein test negative, and was thus found to be fully converted into calcium carbonate.

Further, the diametral tensile strength of the calcium carbonate block was 3.3 MPa and 4.8 MPa, respectively.

FIG. 3 shows a scanning electron microscopic image of the calcium carbonate block of Comparative Example 3 produced by immersing in the sodium hydrogen carbonate aqueous solution for 4 days in the carbonation step.

The comparison between the scanning electron microscopic images of the calcium carbonate block produced using the water-containing calcium hydroxide block in Example 1 (FIG. 2) and the calcium carbonate block produced using the calcium hydroxide block containing substantially no water in Comparative Example 3 (FIG. 3) demonstrated that the powders in the calcium carbonate block produced using the water-containing calcium hydroxide block in Example 1 were bridged at a wide area by precipitates, whereas the bridge brought about by precipitates was limited in the calcium carbonate block produced using the calcium hydroxide block containing substantially no water in Comparative Example 3.

The mechanical strength in terms of diametral tensile strength was 4.8 MPa in Comparative Example 3 and, by contrast, was 8.2 MPa in Example 1, demonstrating that the mechanical strength of the produced calcium carbonate block was significantly increased by using the water-containing calcium hydroxide block rather than the calcium hydroxide compact containing substantially no water.

Example 3

<Calcium Hydroxide Block Shaping Step>

Calcium hydroxide (manufactured by Wako Pure Chemical Industries, Ltd.) and distilled water were mixed at a water/powder mixing ratio of 1.0. The mixture was uniaxially press-shaped at 5 MPa using a mold to shape a calcium hydroxide compact having a diameter of 6 mm and a height of 3 mm. A portion of water was discharged during the uniaxial pressurization. The water content ratio of the shaped calcium hydroxide block was 35% by weight.

<Pre-Carbonation Step>

The pre-carbonation step was not performed.

<Carbonation Step>

The calcium hydroxide block containing water was immersed in a 80° C. 1 mol/L sodium hydrogen carbonate aqueous solution for 4 days. Then, the block was rinsed with distilled water, and washed by immersing in 80° C. distilled water for 24 hours. Further, the block was dried at 60° C. for 24 hours.

The rate of carbonation of the calcium hydroxide block thus immersed for 4 days was 100% by mol. The block was phenolphthalein test negative. Thus, the block was found to be fully converted into calcium carbonate in which no calcium hydroxide remained.

The diametral tensile strength of the block was 1.1 MPa. The scanning electron microscopic image demonstrated that the powders were bridged at a wide area by precipitates.

The block obtained in this Example had sufficient strength, in spite of relatively high porosity.

Example 4

<Calcium Hydroxide Block Shaping Step>

Calcium hydroxide (manufactured by Wako Pure Chemical Industries, Ltd.) and distilled water were mixed at a water/powder mixing ratio of 1.0. The mixture was uniaxially press-shaped at 5 MPa using a mold to shape a calcium hydroxide compact having a diameter of 6 mm and a height of 3 mm. A portion of water was discharged during the uniaxial pressurization. The water content ratio of the shaped calcium hydroxide block was 35% by weight.

(Pre-Carbonation Step)

The produced calcium hydroxide block was carbonated for 10 minutes with carbon dioxide having a relative humidity of 100% using a carbon dioxide contact apparatus.

<Carbonation Step>

The calcium hydroxide block containing water was immersed in a 80° C. 1 mol/L sodium hydrogen carbonate aqueous solution for 4 days. Then, the block was rinsed with distilled water, and washed by immersing in 80° C. distilled water for 24 hours. Further, the block was dried at 60° C. for 24 hours.

The rate of carbonation of the calcium hydroxide block thus immersed for 4 days was 100% by mol. The block was phenolphthalein test negative. Thus, the block was found to be fully converted into calcium carbonate in which no calcium hydroxide remained.

The diametral tensile strength of the block was 1.5 MPa. The scanning electron microscopic image demonstrated that the powders were bridged at a wide area by precipitates.

The block obtained in this Example had sufficient strength, in spite of relatively high porosity.

The comparison between the results of Example 3 and Example 4 demonstrated that a carbonate apatite block having larger mechanical strength can be produced by pre-carbonation.

The comparison of the results of Example 1 with the results of Example 3 and Example 4 demonstrated that a calcium carbonate block having larger mechanical strength can be produced at a higher powder compacting pressure of calcium hydroxide.

Comparative Example 4

<Calcium Hydroxide Block Shaping Step>

Calcium hydroxide (manufactured by Wako Pure Chemical Industries, Ltd.) was uniaxially press-shaped at 5 MPa using a mold to shape a calcium hydroxide compact containing substantially no water and having a diameter of 6 mm and a height of 3 mm. The water content ratio of the shaped calcium hydroxide block was 0.4% by weight.

<Pre-Carbonation Step>

The pre-carbonation step was not performed.

<Carbonation Step>

The calcium hydroxide block containing substantially no water was immersed in a 80° C. 1 mol/L sodium hydrogen carbonate aqueous solution.

The calcium hydroxide block disintegrated immediately after the immersion.

The comparison of the results of Comparative Example 4 with the results of Examples 3 and 4 demonstrated that the calcium hydroxide block containing substantially water disintegrates when immersed in the carbonate ion-containing aqueous solution without pre-carbonation, whereas the water-containing calcium hydroxide block does not disintegrate by immersing in the carbonate ion-containing aqueous solution, and can therefore produce the calcium carbonate block.

Example 5

<Pore-Forming Substance Mixing Step>

Sodium chloride (manufactured by Wako Pure Chemical Industries, Ltd.) was sieved to produce 212 to 300 μm sodium chloride. Next, the sodium chloride was mixed at a weight ratio of 1:1 to a mixture of calcium hydroxide (manufactured by Wako Pure Chemical Industries, Ltd.) and distilled water mixed at a water/powder mixing ratio of 1.0.

<Calcium Hydroxide Block Shaping Step>

The mixture was uniaxially press-shaped at 20 MPa using a mold to shape a calcium hydroxide compact having a diameter of 6 mm and a height of 3 mm. A portion of water was discharged during the uniaxial pressurization. The water content ratio of the shaped calcium hydroxide block was 10% by weight.

(Pre-Carbonation Step)

The produced calcium hydroxide block was carbonated for 1 hour with carbon dioxide having a relative humidity of 100% using a carbon dioxide contact apparatus.

<Carbonation Step>

The calcium hydroxide block containing water was immersed in a 80° C. 1 mol/L sodium hydrogen carbonate aqueous solution for 4 days.

(Pore Formation Step)

After carbonation step, the block was rinsed with distilled water, and washed by immersing in 80° C. distilled water for 24 hours. Further, the block was dried at 60° C. for 24 hours.

The rate of carbonation of the calcium hydroxide block thus immersed for 4 days was 100% by mol. The block was phenolphthalein test negative. Thus, the block was found to be fully converted into calcium carbonate in which no calcium hydroxide remained.

FIG. 4 shows the cross section of the porous calcium carbonate block produced in Example 5.

It can be seen from the scanning electron microscopic image that the porous calcium carbonate was produced.

Comparative Example 5

<Pore-Forming Substance Mixing Step>

The 212 to 300 μm sodium chloride produced in Example 5, and calcium hydroxide (manufactured by Wako Pure Chemical Industries, Ltd.) were mixed at a weight ratio of 1:1.

<Calcium Hydroxide Block Shaping Step>

The mixture was uniaxially press-shaped at 20 MPa using a mold to shape a calcium hydroxide compact having a diameter of 6 mm and a height of 3 mm. The water content ratio of the shaped calcium hydroxide block was 0.2% by weight.

<Carbonation Step>

The calcium hydroxide block was immersed in a 80° C. 1 mol/L sodium hydrogen carbonate aqueous solution. The block started to disintegrate immediately after the immersion and failed to maintain its morphology.

The invention claimed is:

1. A method for producing a calcium carbonate block, comprising:
    shaping a water-containing calcium hydroxide block, wherein the water-containing calcium hydroxide block contains from 4% by weight to 70% by weight of water; and
    immersing the water-containing calcium hydroxide block in a carbonate ion-containing aqueous solution to make the calcium carbonate block.

2. The method for producing a calcium carbonate block according to claim 1, comprising, after shaping the water-containing calcium hydroxide block and before immersing the water-containing calcium hydroxide block in the carbonate ion-containing aqueous solution,
    contacting the water-containing calcium hydroxide block with carbon dioxide to make a partially carbonated calcium hydroxide block.

3. The method for producing a calcium carbonate block according to claim 1, comprising:
    mixing a calcium hydroxide for shaping the water-containing calcium hydroxide block with a pore-forming substance.

4. The method for producing a calcium carbonate block according to claim 1, wherein the water-containing calcium hydroxide block contains from 8% by weight to 70% by weight of water.

5. The method for producing a calcium carbonate block according to claim 1, wherein a volume of the calcium carbonate block is $10^{-13}$ m$^3$ or larger.

6. The method for producing a calcium carbonate block according to claim 1, wherein the carbonate ion-containing aqueous solution contains carbonate ion having a concentration of 0.1 mol/L or more.

7. The method for producing a calcium carbonate block according to claim 1, wherein pH of the carbonate ion-containing aqueous solution is 6 or higher.

8. A method for producing a carbonate apatite block, comprising imparting a phosphate solution to a calcium carbonate block produced by the method according to claim 1.

9. A method for producing a carbonate apatite block, comprising imparting a phosphate solution to a calcium carbonate block produced by the method according to claim 2.

10. A method for producing a carbonate apatite block, comprising imparting a phosphate solution to a calcium carbonate block produced by the method according to claim 3.

11. A method for producing a calcium carbonate block, comprising:
    shaping a water-containing calcium hydroxide block, wherein the water-containing calcium hydroxide block contains 4% by weight or more of water; and
    immersing the water-containing calcium hydroxide block in a carbonate ion-containing aqueous solution to make the calcium carbonate block,
    wherein the water-containing calcium hydroxide block is not contacted with carbon dioxide, after shaping the water-containing calcium hydroxide block and before immersing the water-containing calcium hydroxide block in the carbonate ion-containing aqueous solution.

* * * * *